United States Patent
Stamnes et al.

(10) Patent No.: US 9,823,189 B2
(45) Date of Patent: Nov. 21, 2017

(54) OPTICAL METHOD FOR DETERMINING MORPHOLOGICAL PARAMETERS AND PHYSIOLOGICAL PROPERTIES OF TISSUE

(75) Inventors: Jakob J. Stamnes, Oslo (NO); Knut Stamnes, Maplewood, NJ (US); Lu Zhao, Bergen (NO); Boerge Hamre, Sandsli (NO); Gennady Ryzhikov, Loddefjord (NO); Marina Biryulina, Loddefjord (NO); Endre R. Sommersten, Bergen (NO); Kristian Pagh Nielsen, Copenhagen (DK); Johan E. Moan, Oslo (NO)

(73) Assignee: Balter, AS., Bergen (NO)

( * ) Notice: Subject to any disclaimer, the term of this patent is extended or adjusted under 35 U.S.C. 154(b) by 1141 days.

(21) Appl. No.: 12/933,037

(22) PCT Filed: Mar. 18, 2009

(86) PCT No.: PCT/US2009/037511
§ 371 (c)(1),
(2), (4) Date: Nov. 15, 2010

(87) PCT Pub. No.: WO2009/117485
PCT Pub. Date: Sep. 24, 2009

(65) Prior Publication Data
US 2011/0054298 A1    Mar. 3, 2011

Related U.S. Application Data

(60) Provisional application No. 61/037,503, filed on Mar. 18, 2008.

(51) Int. Cl.
*A61B 6/00*    (2006.01)
*G01N 21/47*    (2006.01)
(Continued)

(52) U.S. Cl.
CPC ....... *G01N 21/4738* (2013.01); *A61B 5/0059* (2013.01); *A61B 5/1455* (2013.01);
(Continued)

(58) Field of Classification Search
None
See application file for complete search history.

(56) References Cited

U.S. PATENT DOCUMENTS 5,813,988 A    9/1998  Alfano et al.
6,081,612 A    6/2000  Gutkowicz-Krusin et al.
(Continued)

FOREIGN PATENT DOCUMENTS

JP    2003149136 A    5/2003
JP    2005-192944 A    7/2005
(Continued)

OTHER PUBLICATIONS

Seidenary et al. ("Digital videomicroscopy improves diagnostic accuracy for melanoma"; department of Dermatology, University of Modena; Apr. 10, 1998).*

(Continued)

*Primary Examiner* — Amanda Lauritzen Moher
*Assistant Examiner* — Shahdeep Mohammed
(74) *Attorney, Agent, or Firm* — Brown Rudnick LLP

(57) ABSTRACT

In an embodiment of the present disclosure, an optical method for determining morphological parameters and physiological properties of tissue is presented. The method includes using reflectance measurements from a tissue area for a plurality of wavelengths, using a bio-optical model, using radiative transfer modeling and using a non-linear inversion procedure. The method further includes systematically varying values of the morphological parameters and physiological properties of the tissue and simultaneously varying the inherent optical properties, which are linked to (Continued)

the morphological parameters and the physiological properties of the tissue, until the non-linear inversion procedure returns values for the morphological parameters and the physiological properties of the tissue such that an agreement between the reflectance measurements and reflectances computed by the radiative transfer model, based on the returned morphological parameters and the physiological properties of the tissue values and corresponding inherent optical properties values, reach a predetermined level of accuracy.

10 Claims, 9 Drawing Sheets

(51) Int. Cl.
  *A61B 5/00* (2006.01)
  *A61B 5/1455* (2006.01)
  *G06K 9/00* (2006.01)
  *G06T 7/62* (2017.01)
  *G06T 7/66* (2017.01)

(52) U.S. Cl.
  CPC .......... *A61B 5/444* (2013.01); *G06K 9/00134* (2013.01); *G06T 7/62* (2017.01); *G06T 7/66* (2017.01); *G06T 2207/30024* (2013.01)

(56) References Cited

U.S. PATENT DOCUMENTS

| | | | |
|---|---|---|---|
| 6,208,749 B1 | 3/2001 | Gutkowicz-Krusin et al. | |
| 6,307,957 B1 | 10/2001 | Gutkowicz-Krusin et al. | |
| 6,324,417 B1 | 11/2001 | Cotton | |
| 2001/0032053 A1 | 10/2001 | Hielscher et al. | |
| 2004/0030255 A1 | 2/2004 | Alfano et al. | |
| 2004/0092824 A1* | 5/2004 | Stamnes et al. | 600/473 |
| 2005/0251049 A1* | 11/2005 | Cane et al. | 600/476 |
| 2006/0247532 A1 | 11/2006 | Ramanujam et al. | |
| 2007/0016078 A1* | 1/2007 | Hoyt | A61B 5/0059 600/476 |
| 2007/0142720 A1* | 6/2007 | Ridder | A61B 5/14532 600/336 |
| 2007/0156037 A1* | 7/2007 | Pilon | A61B 5/0059 600/310 |
| 2007/0269804 A1 | 11/2007 | Liew et al. | |
| 2009/0134331 A1* | 5/2009 | Miyamae et al. | 250/339.12 |

FOREIGN PATENT DOCUMENTS

| | | |
|---|---|---|
| JP | 2007190364 A | 8/2007 |
| WO | WO-00/37924 A1 | 6/2000 |
| WO | WO-02/27660 A2 | 4/2002 |
| WO | WO-2006/076810 A1 | 7/2006 |
| WO | WO 2006076810 A1 * | 7/2006 |
| WO | WO 2007026884 A1 * | 3/2007 |
| WO | WO-2009/094623 A2 | 7/2009 |
| WO | WO-2009/117485 A2 | 9/2009 |

OTHER PUBLICATIONS

Chun et al. ("A nonlinear estimation algorithm, and its optical implementation for the target tracking in clutter environment"; SPIE vol. 3961; 2000).*

Jacques et al. ("Internal absorption coefficient and threshold for pulsed laser disruption of melanosomes isolated from retinal pigment epithelium", SPIE vol. 2681, 1996).*

Hannen, Egied J. M. et al. An Image Analysis Study on Nuclear Morphology in Metastasized and Non-metastasized Squamous Cell Carcinomas of the Tongue. Journal of Pathology. 1998, vol. 185, pp. 175-183 See p. 176, col. 1, Line 37—p. 177, col. 2, Line 57.

Rallan, Deepak et. al. Quantitative Discrimination of Pigmented Lesions Using Three-Dimensional High-Resolution Ultrasound Reflex Transmission Imaging. Journal of Investigative Dermatology. Oct. 2006, vol. 127, pp. 189-195 See p. 190, col. 2, Line 1—p. 191, col. 2, Line 16.

Rolston et al. "A Well Collimated Quasi-Continuous Atom Laser". Mar. 4, 2000. http://web.archive.org/web/20000304120946/http://physics.nist.gov/Divisions/Div842/Gp4/AtomOptics/intro.html.

Siegel, A.M., J.J.A. Marota, and D.A. Boas. "Design and evaluation of a continuous-wave diffuse optical tomography system". 1999. Optics Express. vol. 4, No. 8, pp. 287-298.

International Search Report for PCT/US2009/031969 dated Sep. 1, 2009.

International Search Report for PCT/US2009/037511 dated Dec. 2, 2009.

Notice of Reasons for Rejection in related Japanese application JP2011500922, dated Nov. 19, 2013 [Translation].

Iyatomi et al., 2006, Quantification of clinical items of dermoscopy for computer-based melanoma diagnosis, Proceedings of the Fuzzy System Symposium (CD-ROM) 22:387-392.

Claridge E et al: "Shape Analysis for Classification of Malignant Melanoma", Journal of Biomedical Engineering, Butterworth, Guildford, GB, vol. 14, No. 3, May 1992 (May 1992), pp. 229-234.

Extended European Search Report dated Nov. 30, 2015 for European Patent Application No. 15186132.5 (9 Pages).

Ganster H et al: "Automated Melanoma Recognition", IEEE Transactions on Medical Imaging, IEEE Service Center, Piscataway, NJ, US, vol. 20, No. 3, Mar. 2001 (Mar. 2001), pp. 233-239.

Sboner A et al: "A Multiple Classifier System for Early Melanoma Diagnosis", Artificial Intelligence in Medicine, vol. 27, No. 1, 2003, pp. 29-44.

Nielsen, Kristian P. et al., "Reflectance Spectra of Pigmented and Nonpigmented Skin in the UV Spectral Region", Photochemistry and Photobiology, vol. 80, No. 3, Jan. 1, 2004, pp. 450-455 (6 Pages).

* cited by examiner

OPTICAL METHOD FOR DETERMINING MORPHOLOGICAL PARAMETERS AND PHYSIOLOGICAL PROPERTIES OF TISSUE

CROSS-REFERENCE TO RELATED APPLICATIONS

This patent application claims priority to U.S. Provisional Application Ser. No. 61/037,503, filed in the U.S. Patent and Trademark Office on Mar. 18, 2008 by Jakob J. Stamnes and Knut Stamnes, the entire contents of these applications being incorporated herein by reference in its entirety.

BACKGROUND

1. Technical Field

The present disclosure relates to an optical method for determining several morphological parameters and physiological properties (hereafter abbreviated MP&PPs) of tissue. In particular, the present disclosure is directed to a method to determine MP&PPs of malignant as well as benign tissue lesions.

2. Description of the Related Art

Malignant melanoma is one of the most rapidly increasing cancers in the world. In the United States alone, the estimated incidence for 2008 is 62,480, which leads to an estimated total of 8,420 deaths per year. Successful treatment of melanoma depends on early detection by clinicians with subsequent surgical removal of tumors. Visual detection has its limitations, even when augmented with dermoscopy, especially with less experienced users. Attempts have thus been made to develop automated devices to assist in the screening of pigmented skin lesions for likelihood of melanoma. Several of these devices have digitalized dermoscopy-related features analyzed by artificial neural networks or support vector machine learning systems.

The optical properties of human skin in the ultraviolet spectral region have been studied for almost one hundred years [Hasselbalch, 1911; Everett et al., 1966], and non-invasive optical methods have been applied to study the physiological state of human skin for at least twenty years [Diffey et al., 1984]. A well-known application is blood-oxymetry, by which a relative blood-oxygenation index can be determined non-invasively from the scattered reflectance or transmittance of light at red and near-infrared (NIR) wavelengths [see e.g. Yaroslavsky et al., 2002]. The reflectance in that spectral region has also been used to determine other physiological properties. For example, the gradient of the reflectance spectrum between 620 nm and 720 nm depends on the total melanin content of the skin [Kollias and Baqer, 1985]. However, variations in the blood concentration, the thicknesses of the skin layers, and the scattering phase function of skin tissue, also affect the reflectance spectrum, and thereby the accuracy of the determination of blood oxygenation and total melanin content. Therefore, it is essential to perform a simultaneous determination of all optically important MP&PPs.

In order to determine tissue optical properties (as opposed to MP&PPs) from spectral reflectance measurements several different inversion schemes have been used, including partial least squares regression [Berger et al., 2000], neural networks [Kienle et al., 1996], fuzzy logic [Dam et al., 1998], and genetic algorithms [Zhang et al., 2005]. In contrast, this invention makes use of a nonlinear inversion scheme based on e.g. optimal estimation theory [Tikhonov, 1977; Twomey, 1977; Tarantola, 1987; Rodgers, 2000], combined with bio-optical models [which provide a link between MP&PPs and inherent optical properties (IOPs)] and accurate radiative-transfer modeling in coupled air-tissue systems. Also, this invention provides a method for deriving a set of additional morphological parameters (MPs) of tissue from reflectance measurements.

SUMMARY

In an embodiment of the present disclosure, an optical method for determining morphological parameters and physiological properties of tissue is presented. The method includes using reflectance measurements from a tissue area for a plurality of wavelengths, using a bio-optical model, using radiative transfer modeling and using a non-linear inversion procedure. The method further includes systematically varying values of the morphological parameters and physiological properties of the tissue and simultaneously varying inherent optical properties. The inherent optical properties are linked to the morphological parameters and the physiological properties of the tissue, until the non-linear inversion procedure returns values for the morphological parameters and the physiological properties of the tissue such that an agreement between the reflectance measurements and reflectances computed by the radiative transfer model, based on the returned morphological parameters and the physiological properties of the tissue values and corresponding inherent optical properties values, reach a predetermined level of accuracy.

In another embodiment of the present disclosure, an optical method for determining morphological parameters of tissue from spectral reflectance measurements of tissue is presented. The method includes obtaining a reflection of an image of a lesion, determining a lesion border from the reflected intensity of the image of the lesion from a visible channel and measuring a size of the lesion. The method further includes obtaining a histogram-width, that gives a measure of inhomogeneity of the reflected intensity of the lesion, capturing a relative moment of inertia of the lesion and determining a center distance representing a physical distance between a geometrical center of the lesion and a center of mass of absorptance. The method also includes determining a fractal dimension of the lesion which describes the complexity of its border, determining an asphericity of the lesion and determining a relative border length of the lesion.

BRIEF DESCRIPTION OF THE DRAWINGS

The objects and features of the present disclosure, which are believed to be novel, are set forth with particularity in the appended claims. The present disclosure, both as to its organization and manner of operation, together with further objectives and advantages, may be best understood by reference to the following description, taken in connection with the accompanying drawings as set forth below:

DETAILED DESCRIPTION OF EXEMPLARY EMBODIMENTS

Figure 1:
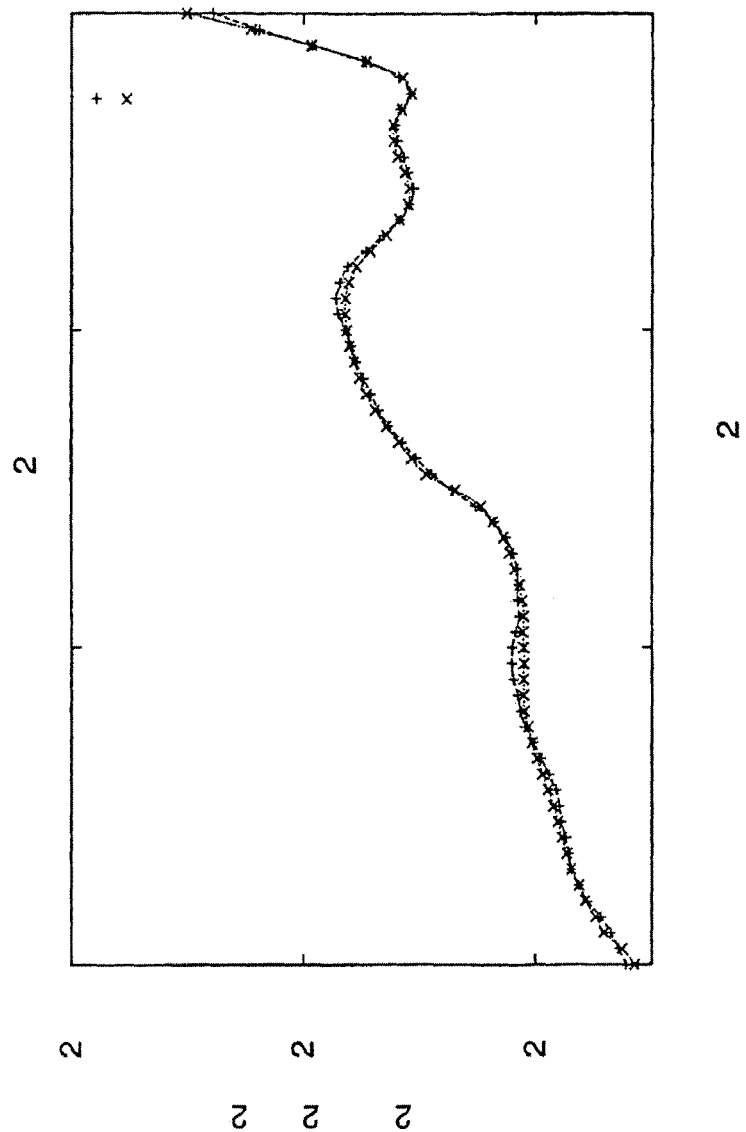
FIG. 1 shows an example of the agreement between measured and simulated reflectance values obtained when using the retrieved values for morphological parameters and physiological properties of the tissue.

The following detailed description refers to the accompanying drawings. The same reference numbers in different drawings may identify the same or similar elements. In addition, the following detailed description does not limit the present disclosure. The present invention relates to a novel method for determining morphological parameters and physiological properties of the tissue (MP&PPs) of different types of tissue lesions. In particular, the present invention is directed to a method for determining MP&PPs for malignant as well as benign tissue lesions. The method of the present invention is applicable to, but not limited to, benign and malignant tissue lesions in general, and uses spectral reflectance measurements of tissue lesions, which may be generated by a spectrophotometer or by an Optical Transfer Diagnosis (OTD) method.

The OTD device currently used records 30 spectral reflectance images of a lesion under examination. These 30 reflectance images, which constitute one image set, are recorded at 10 different wavelengths (365-1.000 nm) from multiple angles of illumination and detection. One version of the OTD device is a spectral reflectance meter consisting of a measurement head 901 with 12 fixed light-emitting diode (LED) lamps 903 and 3 IEEE (Institute of Electrical and Electronics Engineers) 1394 FireWire cameras. Each LED 903 is placed at a different angle relative to the skin 103 to enhance the ability to retrieve information about the depth of the lesion 101. The polar angles of the LEDs 903 vary between 30 and 45 degrees, and the relative azimuth angles between 34 and 145 degrees. The polar angles of the detectors 905 vary between 0 and 45 degrees, and the relative azimuth angles between 0 and 180 degrees. In the current OTD practice, an alcohol-based gel is used as an interface between the measurement probe and the skin 103, and a selected area of the skin 103 is illuminated and imaged through a 2.2 cm diameter circular sapphire plate. The imaging time is approximately 5 seconds.

On the basis of established absorption and transmission spectra for known tissue chromophores and mathematical modeling of spectral tissue reflectance using a bio-optical model in combination with radiative transfer modeling in coupled air-tissue systems, the present invention provides through the use of a non-linear inversion procedure, a method for deriving MP&PPs as well as additional MPs of a lesion from a set of spectral reflectance measurements. By this method, several MP&PPs can be determined including (i) percentage of hemoglobin; (ii) percentage of hemoglobin oxygenation; (iii) upper epidermal thickness; (iv) lower epidermal thickness; (v) percentage of upper melanosome concentration; (vi) percentage of lower melanosome concentration; and (vii) percentage of keratin concentration. The third and fourth of these entities are MPs, while the remaining five entities are physiological properties (PPs) describing the physiological state of the tissue. Each of these seven entities varies and is different for normal and malignant tissues. Also, the present invention provides a method for deriving a set of additional MPs of diagnostic value directly from the reflectance measurements.

It is important to combine information about parameters that characterize the physiological state of the skin tissue with information of diagnostic value obtained from MPs other than the thicknesses of the upper and lower epidermis layers. For example, an unusually high melanin content would not suffice to make a definitive melanoma diagnosis, but if a lesion with high melanin content also had an irregular spatial distribution of the reflected intensity, then the high melanin content could indicate with a higher probability that the lesion might be a melanoma.

To aid the differentiation between benign and malignant tissue, a description of how a lesion can be defined directly from measured reflectance spectra and how such measurements can be used to characterize the lesion in terms of a set of MPs follows. As an example, an aim is to differentiate between benign pigmented nevi and malignant melanomas, but the method is applicable in general to differentiate between benign and malignant tissue.

A lesion border is defined from measured reflectance spectra by using the reflected intensity from one of the channels in the visible spectral range, for example the green channel. As an example, 10 different MPs are descriptive of the lesion and can be used as an aid to make a definitive diagnosis.

Lesion border. The border of a lesion is defined from the reflected intensity of the image from one of the visible channels, for example the green channel, looking straight down at the lesion, by identifying the regions in which the gradient of the reflected intensity has its largest values.

Size: The size parameter $p_{M1}$ is defined as the number of pixels comprising the lesion, i.e. $p_{M1}$ is the number of pixels inside the lesion border defined above.

Histogram width: For a given combination of illumination and observation directions, the histogram-width parameter $p_{M2}$ gives a measure of the inhomogeneity of the reflected intensity of a lesion. Usually this parameter is small for benign nevi, but large for melanomas. Sebhorreic keratoses can also have relatively large inhomogeneities of the reflected intensity.

Relative moment of inertia: For a given combination of illumination and observation directions, the parameter $p_{M3}$ provides information about another aspect of the inhomogeneity of the reflected intensity of a lesion. Let the spatial light absorptance distribution in a lesion be defined as its "mass distribution" and calculate its "center of mass" and "total mass", the latter being defined as the average light absorptance of the lesion. Then the parameter $p_{M3}$ gives the moment of inertia of the lesion relative to that of a homogeneous circular disk having the same "total mass" as the lesion and a diameter equal to the average diameter of the lesion. If there is a high melanin concentration towards the center of a lesion, this parameter will be small, while it will be large if there is a high melanin concentration towards its border. For the melanomas examined so far, the $p_{M3}$ values were small, in particular for well-developed melanomas.

Center distance: The center distance $p_{M4}$, which provides additional information about the asymmetry of the lesion, represents the physical distance between the "geometrical center of a lesion" and the "center of mass" of the absorptance, as defined above. The "geometrical center of a lesion" means its center with respect to its border, irrespective of how the pigment is distributed within it. Thus, if a lesion has an asymmetrical pigment distribution, the distance between the "geometrical center" and the "center of mass" will be significant.

Darkness: The darkness parameter $p_{M5}$ is defined as the average value of the reflected intensity of a lesion.

Fractal dimension: The fractal-dimension parameter $p_{M6}$ describes the complexity of the border of a lesion. It is defined such that the border of a lesion has a fractal dimension of 1 if the lesion border is perfectly smooth, independent of magnification, while the fractal dimension of the lesion border will tend towards 2 if it is highly irregular.

Asphericity: The asphericity parameter $p_{M7}$ is defined as the ratio between the long and short axes of a lesion. It is 1 for a circular lesion, and increases as a lesion gets more elongated. Just as $p_{M6}$ and $p_{M8}$, this parameter depends only on the border of the lesion, and does not contain any information about its internal structure.

Relative border length: The relative border length $p_{M8}$ is defined as the ratio of the border length of a circle with the same area as the lesion to the border length of the lesion.

Size vs. fractal dimension: The parameter $p_{M9}$ is defined as the size divided by the fractal dimension, i.e. $p_{M9}=p_{M1}/p_{M6}$.

Border length vs. fractal dimension: The parameter $p_{M10}$ is defined as the relative border length divided by the fractal dimension, i.e. $p_{M10}=p_{M8}/p_{M6}$.

Multi-spectral reflectance measurements combined with bio-optical models and accurate radiative transfer simulations of light propagation inside tissue and backscattering from it, provide a basis for obtaining estimates of MP&PPs. In order to determine important tissue MP&PPs the following ingredients are needed: 1. A bio-optical model that relates tissue MP&PPs to tissue IOPs, the latter being the absorption and scattering coefficients as well as the scattering phase function, each as a function of wavelength and depth in the tissue; 2. An accurate radiative transfer model for coupled air-tissue systems, which for a given set of IOPs computes various apparent optical properties (AOPs), such as the diffuse reflectance spectrum; 3. An iterative inversion scheme that accounts for the nonlinear dependence of the AOPs on the IOPs.

Commonly used radiative transfer models include one based on the diffusion approximation and another based on Monte Carlo (MC) simulations. The first method is not accurate enough for our purpose, and the MC method is too slow. The numerically stable discrete ordinate radiative transfer (DISORT) model provides accurate results for coupled air-tissue systems in an efficient manner. Thus, the DISORT code for coupled air tissue systems (CAT-DISORT) is several orders of magnitude faster than the MC method and provides results that are just as precise. It includes a bio-optical model that has been applied also to provide estimates of the efficiency of various photobiological processes and photodynamic therapy in the UV and visible spectral regions.

To illustrate the potential of our method for determining tissue MP&PPs, a study was carried out that aimed at evaluating the feasibility of employing the bio-optical model together with CAT-DISORT forward simulations and inversion based on Bayesian optimal estimation to determine important MP&PPs of skin tissue from diffuse reflectance spectra measured by Zhao et al. (2006). The bio-optical model contains a large number of variable MP&PPs that in principle could be retrieved, but most of them were kept fixed while only a few were treated as retrievable entities. Chromophores, such as the epidermal melanosome concentration and the dermal blood concentration, were considered as retrievable entities, since their variability strongly influences the apparent optical properties of the tissue, such as the spectral tissue reflectance. But entities describing the optical properties of the cellular matrix into which the chromophores are embedded, were kept fixed because variations in these entities have little impact on the apparent optical properties of the tissue.

Reflectance spectra in the wavelength region from 300 nm to 600 nm were measured daily from three test areas and three control areas on a volunteer with skin type III for two weeks during which the skin in the test areas went through erythema and pigmentation. The volunteer, who had given his written permission to participate in the study, was healthy and did not use any medical drugs. Erythema and pigmentation were induced after 24-hour topical application of a photosensitizer followed by illumination with red light (632 nm) for 2 minutes on the first day ('day 0') of the experiment. A brief summary of the design of the photodynamic experiment is given below.

Three test areas (A, B & C), each 1 cm×1 cm with approximately 1.5 cm distance between adjacent areas, were marked on the inner part of the right forearm of the volunteer. Cream was prepared using 10% (w/w) of the hexylester of 5-aminol evulinic acid (ALA-Hex) in a standard oil-in-water cream base (Unguentum, Merck, Darmstad, Germany). Freshly prepared cream with approximately (75±10) mg/cm$^2$ of ALA-Hex was topically applied on each of the three test areas, which were subsequently covered with transparent adhesive dressings (OpSite Flexifix, Smith & Nephew Medical Ltd., Hull, UK), in which three openings (1 cm×1 cm) had been cut out precisely in the places where the test areas were located. The dressings were intended to prevent the cream from diffusing to adjacent areas. The creams and the dressings were kept for 24 hours on the test areas, which were then illuminated with red light (632 nm) for 2 minutes.

Three control areas, similar to the test areas, were also marked on the volunteer. On the first of these control areas (D) ALA-Hex was applied but it was not illuminated; the second of the control areas (E) was illuminated with red light, but no ALA-Hex was applied; on the third control area (F) a base cream, without ALA-Hex was applied, and it was illuminated with red light.

A luminescence spectrometer was employed to record reflectance spectra from each of the test areas and each of the control areas. The spectrometer was equipped with two scanning grating monochromators, one in front of the light source (a pulsed Xenon lamp) and another in front of the detector. A fiber-optic probe was coupled to the spectrometer. The probe was a commercially available fiber accessory (Perkin-Elmer), consisting of two 1 m fused silica fiber bundles joined in parallel at the measuring tip. It was connected to a cylindrically shaped aluminum spacer with an inner diameter of 4 mm. The spacer was painted black inside in order to minimize stray light. The spacer was pressed lightly against the skin to keep the probe at a fixed distance of 10 mm above the skin surface. This arrangement ensured a relatively uniform distribution of the excitation light over the area to be examined. Reflectance spectra were measured in synchronous scans in which both gratings were set at the same wavelength and band pass (5 nm) to avoid fluorescence artifacts. The area exposed to the excitation light of the spectrometer was the same as the area from which the reflected light was detected. The geometry of the fiber probe was such that both the directly (Fresnel) reflected and the diffusely reflected irradiances from the skin were collected and recorded. Care was taken not to press the spacer too hard against the skin surface in order to minimize artifacts from pressure-induced reductions in the blood flow.

A coupled air-tissue system can be represented by a layered medium with constant inherent optical properties (IOPs) in each layer. The tissue is assumed to be a turbid layered medium so that radiative transfer theory can be used to compute the diffuse light inside it and reflected from it. Each tissue layer can be described in terms of its IOPs, which are the absorption coefficient $\alpha([mm^{-1}])$, the scattering coefficient $\sigma([mm^{-1}])$, the (normalized) scattering phase function $p(\cos\Theta)$, and the physical thickness $\Delta z$ ([mm]). In terms of $\alpha$, $\sigma$, and $\Delta z$, one may define two non-dimensional IOPs given by $\tau=(\alpha+\sigma)\Delta_z$ (optical thickness) and $\alpha=\sigma/(\alpha+\sigma)$ (single-scattering albedo), so that the IOPs in each layer of the tissue can be adequately described by the two variables $\tau$ and $\alpha$, as well as a third parameter g, related to the scattering phase function.

The scattering phase function gives the distribution of the scattered light as a function of the scattering angle $\Theta$, Skin tissue is a complex medium with many different kinds of scattering 'particles' in each layer, and the scattering phase function for a particular layer represents a weighted mean of scattering phase functions for several types of particles. Different descriptions of the scattering phase function $p(\cos\Theta)$ may be used in different physical and practical applications. Here, two such functions, namely the Henyey-Greenstein scattering phase function $p_{HG}(\cos\Theta)$ and the Rayleigh scattering phase function $p_{Ray}(\cos\Theta)$ are used. A convenient measure of the angular distribution of the scattering is the average over all scattering directions (weighted by $p(\cos\Theta)$) of the cosine of the scattering angle $\Theta$, i.e. ($\mu=\cos\Theta$)

$$\langle\cos\Theta\rangle = g = \frac{1}{2}\int_0^\pi p(\cos\Theta)\cos\Theta\sin\Theta d\Theta = \frac{1}{2}\int_{-1}^1 p(\mu)\mu d\mu. \quad (1)$$

The average cosine g is called the asymmetry factor of the scattering phase function.

In 1941 Henyey and Greenstein proposed the one-parameter scattering phase function given by $$p_{HG}(\cos\Theta) = \frac{1-g^2}{(1+g^2-2g\cos\Theta)^{3/2}} \quad (2)$$

where g is the asymmetry factor [see Eq. (1)]. This Henyey-Greenstein scattering phase function has no physical basis, but is useful for describing scattering by large particles in a medium, such as tissue, for which the actual scattering phase function is unknown. Here, the term 'large particles' implies that their sizes are comparable to or larger than the wavelength. When the size d of the scatterers is small compared with the wavelength of light $$\left(d<\frac{1}{10}\lambda\right),$$

the Rayleigh scattering phase function gives a good description of the angular distribution of the scattered light. The Rayleigh scattering phase function for unpolarized light is given by $$p(\cos\Theta) = \frac{3}{4+f}(1+f\cos^2\Theta) \quad (3)$$

where f is a polarization factor. Originally, the Rayleigh scattering phase function was derived for scattering of light by an electric dipole. Since the Rayleigh scattering phase function is symmetric about $\Theta=90°$, the asymmetry factor is g=0. However, unlike the Heney-Greenstein scattering phase function [Eq. (2)], which gives isotropic scattering for g=0, the Rayleigh scattering phase function does not represent, isotropic scattering.

A bio-optical model was used to calculate the IOPs for a given set of MP&PPs that describe the physiological state of the tissue. In order to calculate the AOPs (in this case the diffuse reflectance spectrum from the tissue), the CAT-DISORT was employed to solve the radiative transfer equation for a slab of biological tissue stratified into a number of layers, thereby accounting for the reflection and refraction of the incident radiance at the air-tissue interface (caused by the change in the refractive index), which affect the radiation field significantly. An integral part of the forward-inverse modeling procedure was to couple the bio-optical model to CAT-DISORT in such a way that the MP&PPs could be determined directly from the measured AOPs.

In order to obtain a unique solution of our inverse or retrieval problem, most MP&PPs are kept fixed, while other MP&PPs are considered to be retrievable, and therefore allowed to vary. The following 7 retrievable MP&PPs varied:

The dermal blood content
The percentage of oxygenated blood
The melanosome concentration in the lower epidermis
The thickness of the lower epidermis
The melanosome concentration in the upper epidermis
The thickness of the upper epidermis
The keratin concentration in the upper epidermis.

The other MP&PPs were fixed. Thus, each of the scattering coefficients associated with the non-pigmented constituents of the epidermis and the dermis, the optical thickness of the dermis, and the optical properties of the subcutaneous layer were assumed to be fixed.

FIG. 1 shows an example of the agreement between measured and simulated reflectance values obtained when using the retrieved values for the 7 MP&PP entities listed above as inputs to CAT-DISORT simulations. In FIG. 1, measured (+) and simulated (×) reflectance spectra for test area A on the seventh day after the photodynamic exposure is shown. The figure shows that good agreement was obtained between measured and simulated spectra when the 7 retrieved MP&PPs for this day were used as inputs to CAT-DISORT simulations.

FIGS. 2-8 show the retrieved values of the blood content in the dermis (FIG. 2), the percentage of oxygenated blood (FIG. 3), the melanosome concentration in the lower layer of the epidermis (FIG. 4), the melanosome concentration in the upper layer of the epidermis (FIG. 5), the thickness of the lower epidermis (FIG. 6), the thickness of the upper epidermis (FIG. 7), and the keratin concentration in the upper epidermis (FIG. 8), respectively. The three panels in the left column of each figure represent the test areas (A-C), while the three panels in the right column represent the control areas (D-F). In the bio-optical model for tissue the epidermis was divided into five layers and the melanosome concentration was allowed to vary from one layer to another. Here, the epidermis is divided into two layers and the melanosome concentration and the thickness for each of them are retrieved.

Figure 2:
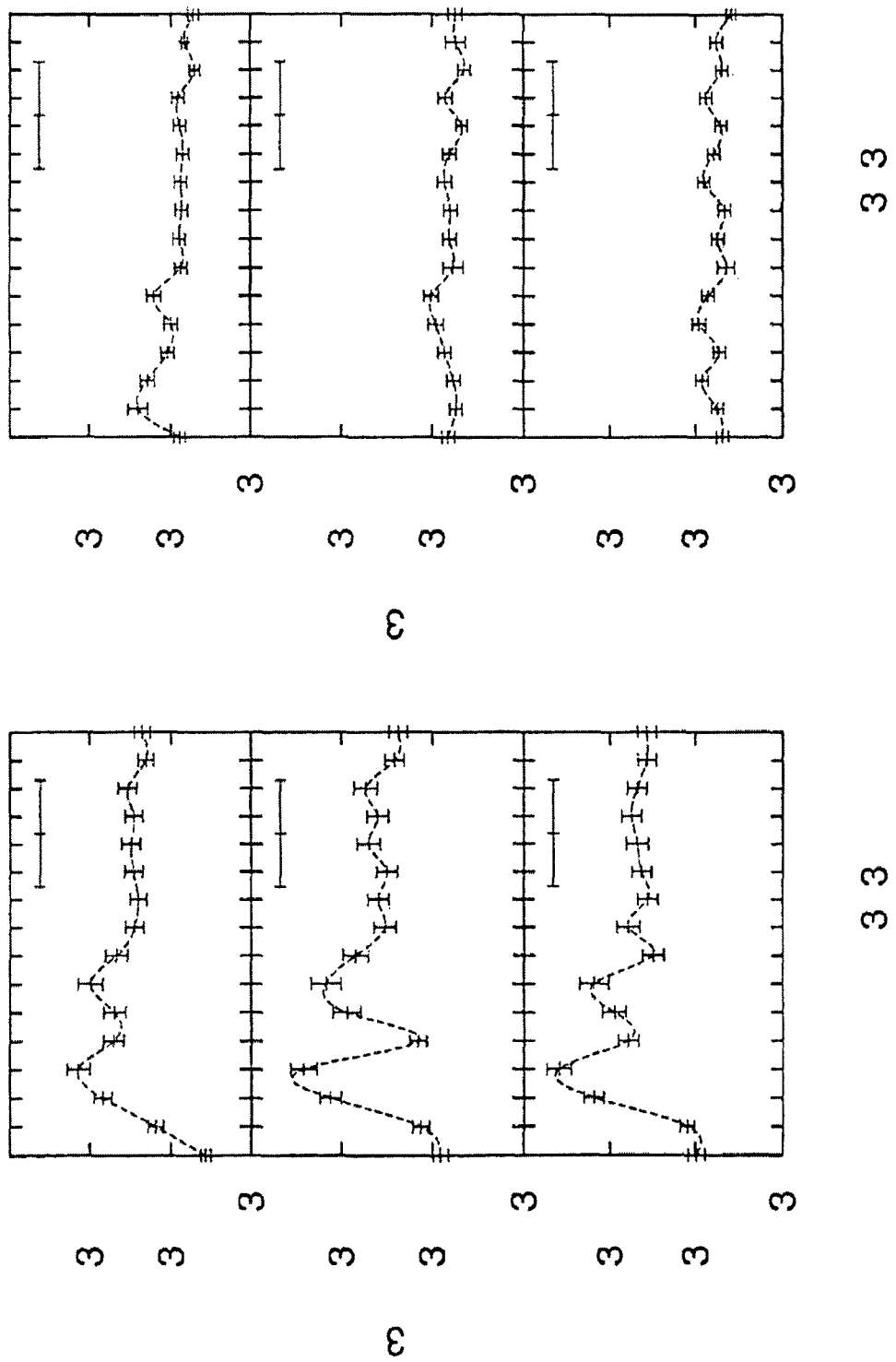
FIG. 2 shows the retrieved dermal blood concentration for each of the measurement areas.

In FIG. 2, retrieved dermal blood concentration for each of the measurement areas for the 15 days of measurement is shown. 'Initial' refers to the situation prior to the photodynamic treatment of the skin, while the next tick mark refers to the situation immediately after the photodynamic treatment.

Figure 3:
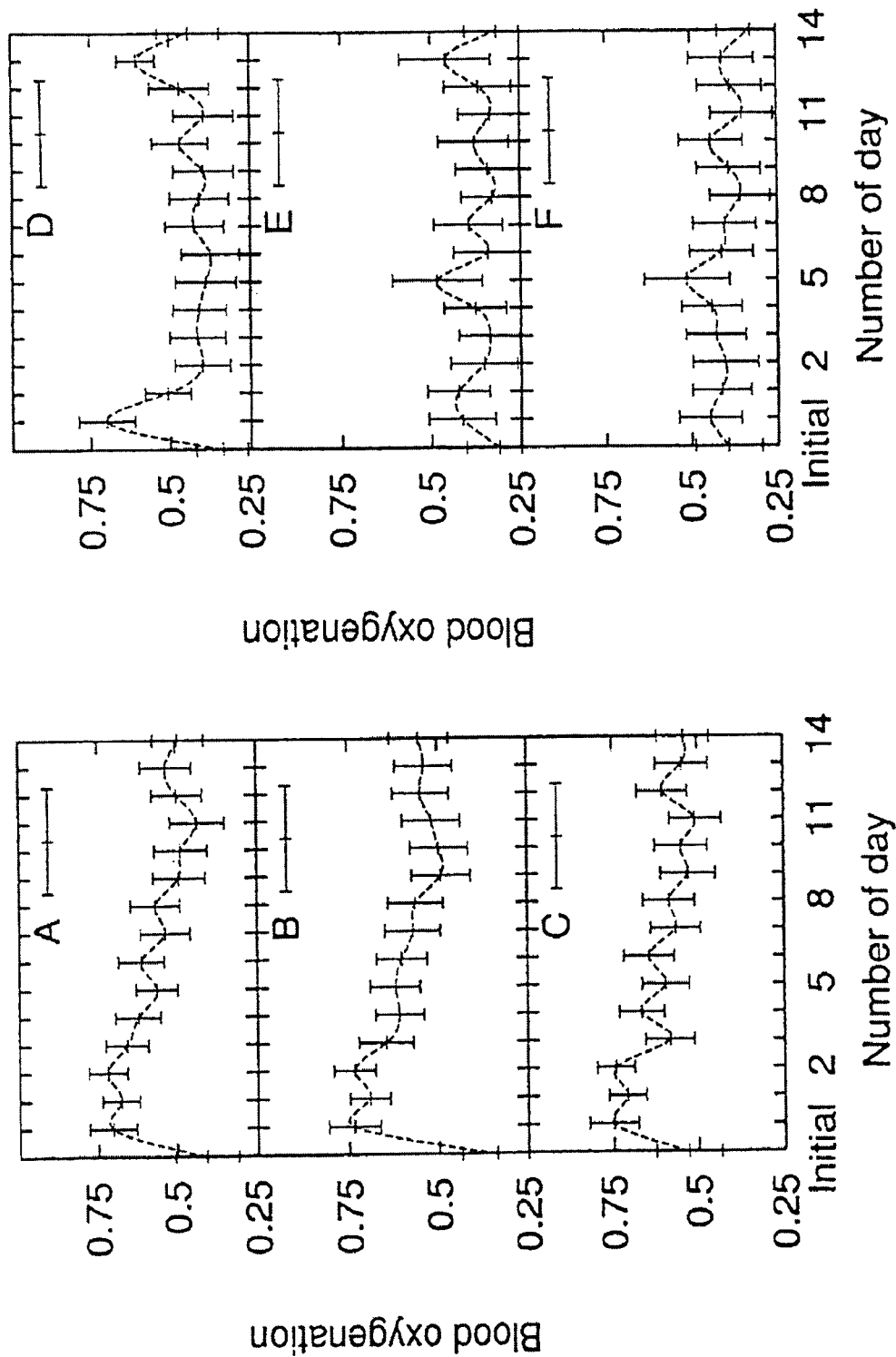
FIG. 3 shows the retrieved percentage of oxygenated blood for each of the measurement areas.

In FIG. 3, retrieved percentage of oxygenated blood for each of the measurement areas for the 15 days of measurement is shown. 'Initial' refers to the situation prior to the photodynamic treatment of the skin, while the next tick mark refers to the situation immediately after the photodynamic treatment.

Figure 4:
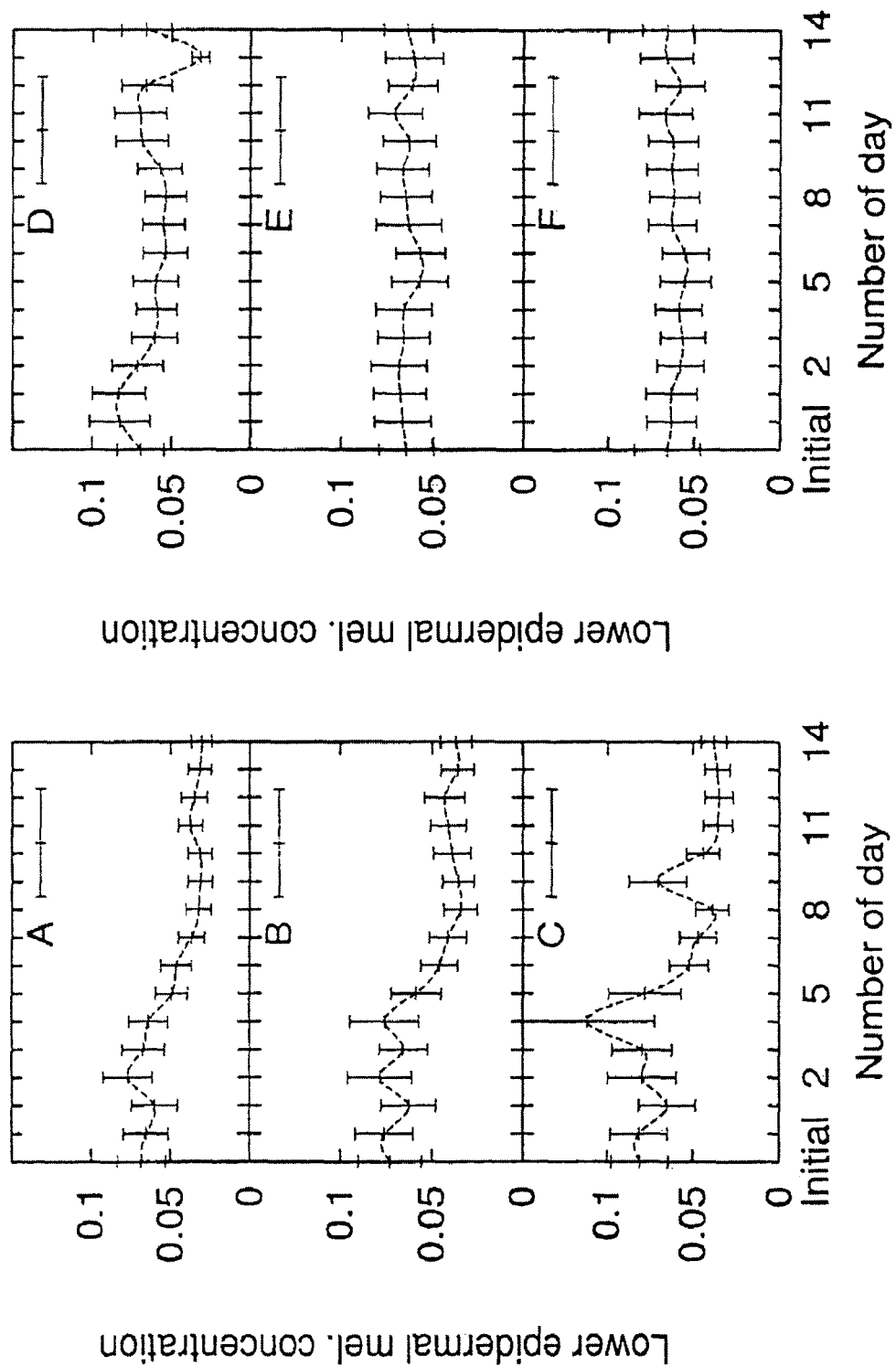
FIG. 4 shows retrieved melanosome content in the lower epidermis for each of the measurement areas.

In FIG. 4, retrieved melanosome content in the lower epidermis for each of the measurement areas for the 15 days of measurement is shown. 'Initial' refers to the situation prior to the photodynamic treatment of the skin, while the next tick mark refers to the situation immediately after the photodynamic treatment.

Figure 5:
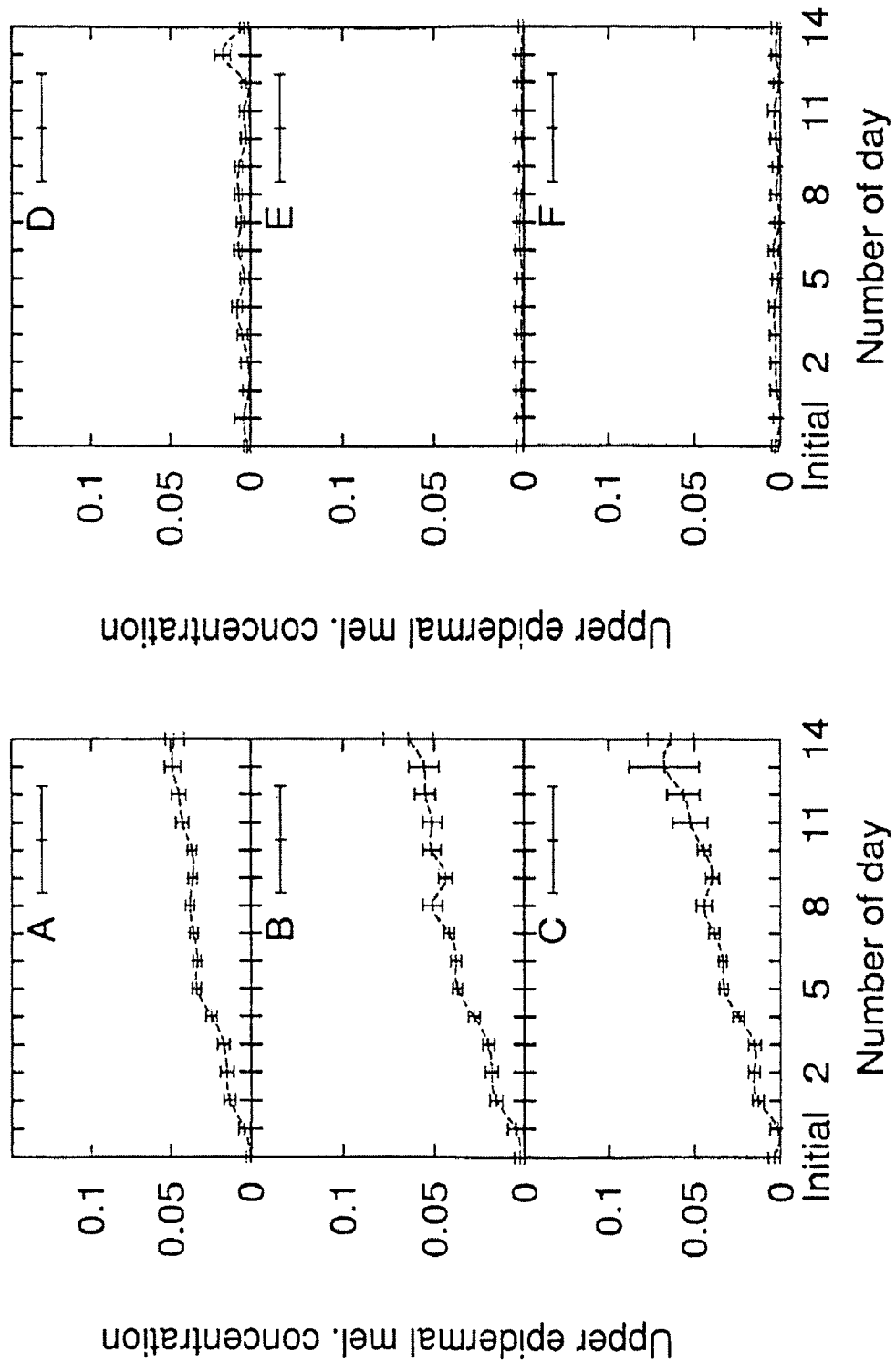
FIG. 5 shows retrieved melanosome content in the upper epidermis for each of the measurement areas.

In FIG. 5, retrieved melanosome content in the upper epidermis for each of the measurement areas for the 15 days of measurement is shown. 'Initial' refers to the situation prior to the photodynamic treatment of the skin, while the next tick mark refers to the situation immediately after the photodynamic treatment.

Figure 6:
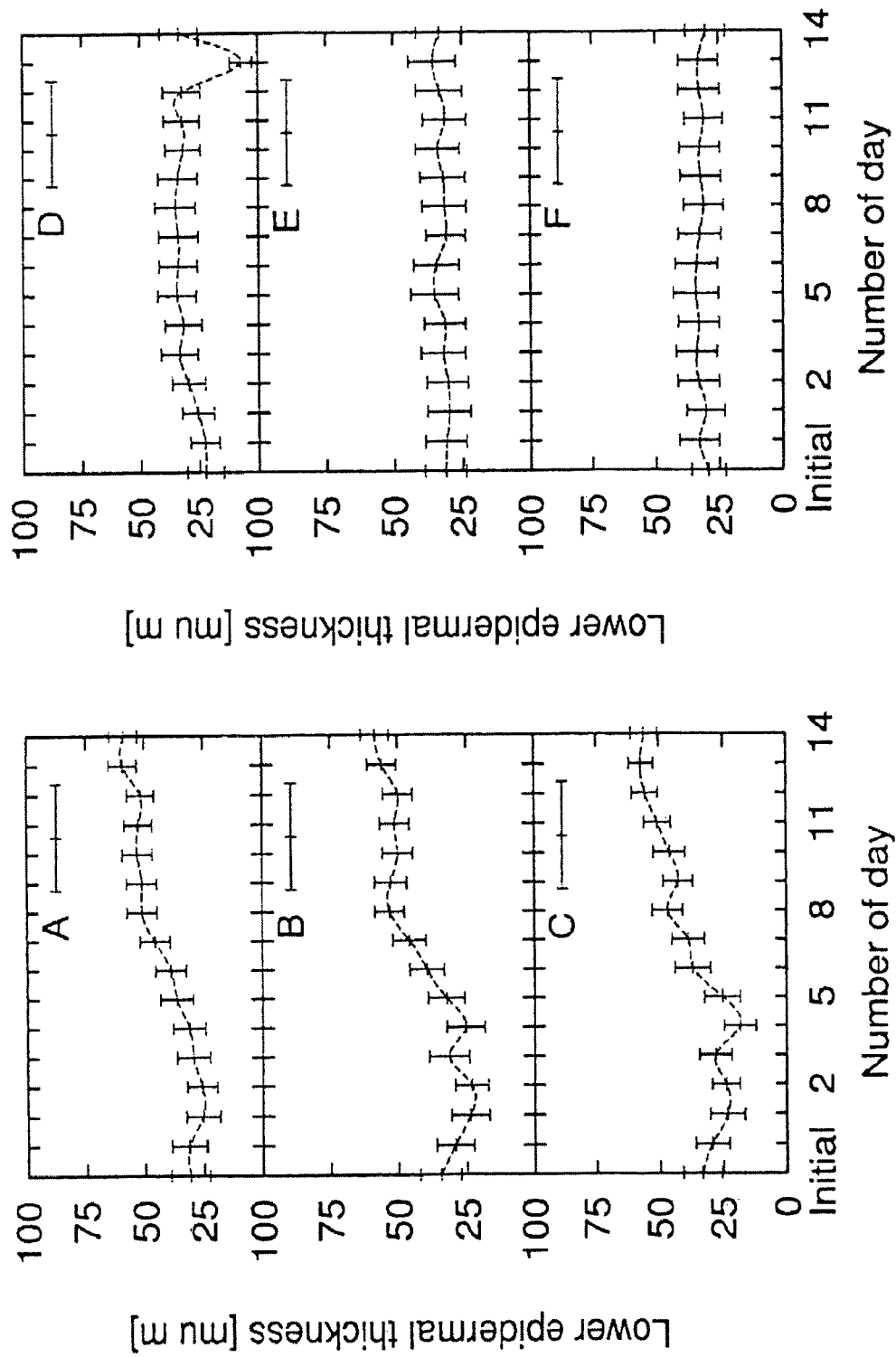
FIG. 6 shows retrieved lower epidermis thickness for each of the measurement areas.

In FIG. 6, retrieved lower epidermis thickness for each of the measurement areas for the 15 days of measurement is shown. 'Initial' refers to the situation prior to the photodynamic treatment of the skin, while the next tick mark refers to the situation immediately after the photodynamic treatment.

Figure 7:
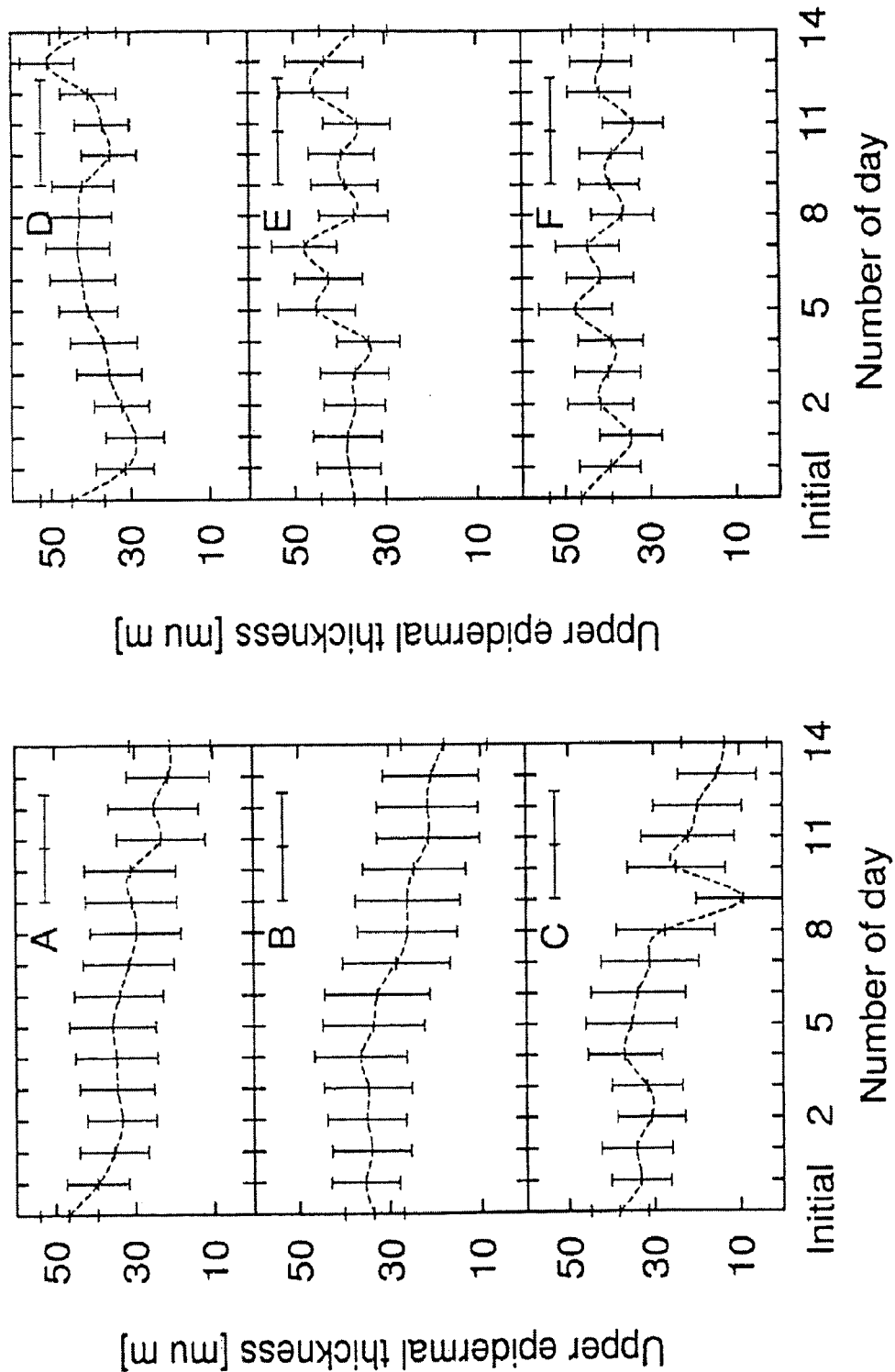
FIG. 7 shows retrieved upper epidermis thickness for each of the measurement areas.

In FIG. 7, retrieved upper epidermis thickness for each of the measurement areas for the 15 days of measurement is shown. 'Initial' refers to the situation prior to the photodynamic treatment of the skin, while the next tick mark refers to the situation immediately after the photodynamic treatment.

Figure 8:
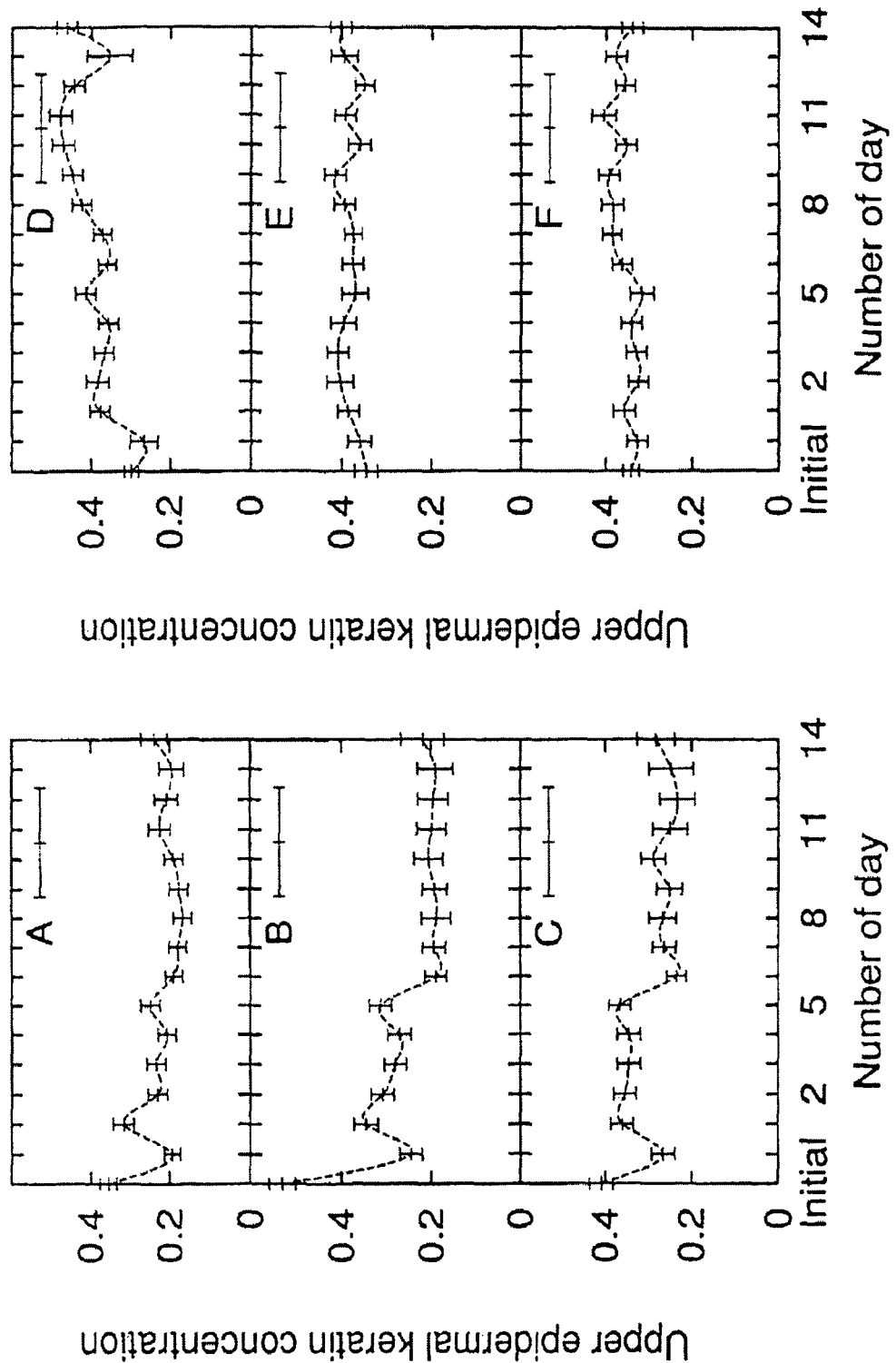
FIG. 8 shows retrieved epidermal keratin content for each of the measurement areas.
Figure 9:
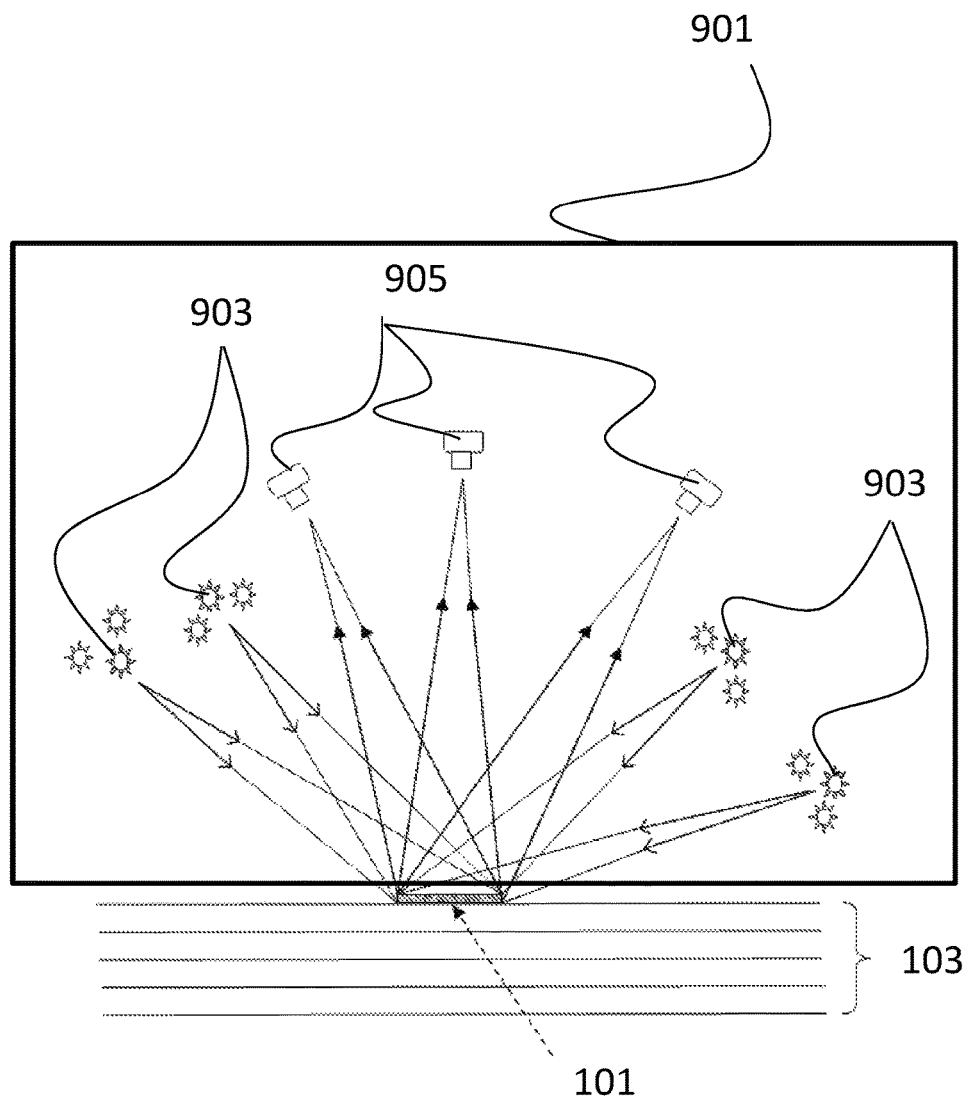
FIG. 9 shows an exemplary Optical Transfer Diagnosis (OTD) device.

In FIG. 8, retrieved epidermal keratin content for each of the measurement areas for the 15 days of measurement is shown. 'Initial' refers to the situation prior to the photodynamic treatment of the skin, while the next tick mark refers to the situation immediately after the photodynamic treatment.

The standard deviations or the error bars that are shown in FIGS. 2-8 were calculated during the retrieval procedure from the diagonal elements of the covariance matrix $[\Phi_{final}]^{-1}$ as defined in Eq. (19) below and explained in the discussion that follows Eq. (19). In general, the temporal variation in the blood content of the tissue (FIG. 2) was in good agreement with expectations. A maximum was reached after 1-2 days, the so-called erythema reaction, typical for sunburn, after which the blood content slowly decayed. This pattern is similar for the three test areas. For the three control areas the variations are within the range of the calculated standard deviations.

FIG. 3 shows the percentage of oxygenated blood immediately after the photodynamic treatment and during the following two weeks for the six measurement areas. Photodynamic therapy is known to be an oxygen consuming process. Thus, it must be emphasized that 'immediately after' means several seconds or may be even a minute after the exposure. The marked increase in oxygenation measured at the beginning of the experiment, at all the three test areas, is likely to be a reaction to the photodynamic treatment, rather than a direct effect of the treatment itself. The variation in blood oxygenation at the three control areas is of a stochastic nature.

The relative change of the percentage of oxygenated blood during the two weeks of measurements seems reasonable. However, the absolute values, which are in the range between 40% and 80%, may be too low. (FIG. 3). These low oxygenation percentages could be caused by the bandpass of the spectrometer (5 nm) being insufficiently narrow to resolve the spectral fine structure in the 540 nm-580 nm spectral region. The skin reflectance in this spectral region is very sensitive to the percentage of oxygenated blood. Therefore, the percentage of oxygenated blood could be underestimated from these measurements.

The retrieval of the melanosome content was less uncertain for the upper epidermis (FIG. 5) than for the lower epidermis (FIG. 4). Thus, the standard deviations for the lower epidermal melanosome content were about twice as large as for the upper epidermal melanosome content.

For the three test areas, the melanosome content in the lower epidermis decreased during the two weeks (FIG. 4), while the melanosome content in the upper epidermal layer increased, in particular during the first week (FIG. 5). This behaviour is similar to that caused by pigmentation induced by UVB radiation (with wavelengths shorter than 320 nm). Thus, as a reaction to UVB exposure the melanosome pigment particles tend to be transferred from the melanocytes in the basal layer of the epidermis to the keratinocytes in the upper layer. In the experiment discussed here, there was no sign of immediate pigment darkening, a process primarily induced by UVA radiation (with wavelengths longer than 320 nm). Had immediate pigment darkening occurred, it would have been seen in the measurements taken immediately after the photodynamic treatment.

Hence, the photodynamic process induced by topical application of ALA-Hex followed by illumination with red light (632 nm wavelength) bears similarities with the photobiological pigmentation process induced by UVB radiation, but immediate melanin darkening does not take place during PDT.

The decrease in the retrieved lower melanosome concentration occurs simultaneously with an increase in the retrieved lower epidermal thickness. Thus, the total retrieved lower epidermal melanosome content turned out to be fairly constant during the two weeks of measurements. No significant temporal variations were found in the control areas in either the retrieved lower or upper epidermal melanosome concentrations (FIGS. 4 & 5) or in the retrieved lower or upper epidermal thickness (FIGS. 6 & 7).

The retrieved thickness of the total epidermis is close to what would be expected. Thus, Sandby-Møller et al. (2003) performed measurements on the dorsal forearm of 71 volunteers and found the average epidermal thickness to be 76 µm±15 µm. As can be seen from FIGS. 6 & 7, a total epidermal thickness of approximately 70 µm for both the test sites and the control sites was retrieved. Thus, the epidermal thickness appears to be retrieved well from the measurements.

It is feasible to perform accurate retrievals of several key MP&PPs describing the physiological state of human skin tissue by using an accurate radiative transfer model for the coupled air-tissue system as a forward model in conjunction with a bio-optical model and a nonlinear inversion scheme.

Retrievals made from analyses of diffuse reflectance spectra measured before and after the exposure of the skin to ALA-Hex photodynamic treatment (PDT) with red light, and on each day for two weeks after that PDT exposure provided results in good agreement with those obtained in previous investigations of UVB-induced erythema and pigmentation in human skin:

The erythema maximizes 1-2 days after the ALA-Hex PDT exposure and then subsides;

There is a strong increase in the pigmentation of the upper epidermal layers, in particularly during the first 7 days after the ALA-Hex PDT exposure;

The blood oxygenation is found to increase immediately after the exposure and then return to pre-exposure values more than seven days later.

The process induced in the skin by ALA-Hex PDT with red light thus appears to be similar to the process induced by UVB radiation.

These results represent the first simultaneous quantitative retrievals of the melanosome concentrations in the upper and the lower epidermis, the epidermal keratin concentration, the dermal blood concentration, and the percentage of oxygenated blood.

In a forward model, an assumption may be made that tissue may be modeled as a turbid, plane-parallel, vertically inhomogeneous, layered medium with specified optical properties. Thus, the inherent optical properties (IOPs), i.e., the absorption coefficient $\alpha(z)$, the scattering coefficient $\sigma(z)$ and the normalized scattering phase function $p(z,\Theta)$ were allowed to vary with depth z in the tissue. Here, $\Theta$ is the scattering angle, and the differential optical depth for a thin layer of thickness dz is $d\tau=-(\alpha(z)+\sigma(z))dz$. Lateral variations in the IOPs may be ignored, keeping in mind that every measured value corresponds to the radiance reflected by the tissue into the upper hemisphere and then gathered by the finite aperture of an optical system.

The integro-differential equation of radiative transfer describing light propagation in such a medium can be written in the form:

$$u\frac{dI(\tau, u, \phi)}{d\tau} = I(\tau, u, \phi) - J(\tau, u, \phi) \quad (4)$$

where the source function is given by $$J(\tau, u, \phi) = \frac{a(\tau)}{4\pi}\int_0^{2\pi} d\phi' \int_{-1}^{1} du' p(\tau, u, \phi; u', \phi') I(\tau, u', \phi') + Q(\tau, u, \phi). \quad (5)$$

Here $I(\tau,u,\phi)$ stands for the diffuse radiance, u is the cosine of the polar angle $\theta$, and $\phi$ is the azimuth angle. The angles $(\theta',\phi')$ denote the direction of a beam of light before a scattering event and the angles $(\theta,\phi)$ denote the observation direction. The scattering angle $\Theta$ between these two directions is given by $$\cos\Theta = \cos\theta\cos\theta' + \sin\theta\sin\theta'\cos(\phi'-\phi).$$

The first term in the source function $J(\tau,u,\phi)$ represents multiple scattering, $\alpha(\tau)=\sigma(\sigma)/[\alpha(\tau)+\sigma(\tau)]$ denotes the single-scattering albedo, and $$Q(\tau, u, \phi) = \frac{a(\tau)}{4\pi} p(\tau, u, \phi; -\mu_0, \phi_0) S_b(\tau) \exp(-\tau/\mu_0) \quad (6)$$

describes the incident beam of irradiance $S_b$ in direction $(-\mu_0,\phi_0)$ with $\mu_0 \equiv^{602} \delta i_0{}^\circ \delta \equiv^\circ \delta \cos\theta_1{}^\circ i$, where $\theta_0$ is the polar angle of the incident beam. The probability of scattering an angle $\Theta$ from the direction $(\theta',\phi')$ into the direction $(\theta,\phi)$ is described by the scattering phase function $p(\tau, \cos\Theta)=p(\tau, u,\phi; u',\phi')$, whose first moment or asymmetry parameter, is given by ($\mu=\cos\Theta$)

$$g(\tau) = \frac{1}{2}\int_{-1}^{1} \mu p(\tau, \mu) d\mu,$$

as in Eq. (1). To quantify the propagation of UV and visible light in a turbid layered medium with known IOPs, as well as the diffuse reflectance spectra (apparent optical properties: AOPs), the CAT-DISORT (Coupled Air-Tissue DIScrete-Ordinate Radiative Transfer) model is used to solve Eq. (4). Thus, the IOPs were used as input to the CAT-DISORT model to compute the reflected radiances (AOPs) in directions $(\theta_a,\phi_a)$ inside the detector aperture. To simulate measurement values the computed radiances were integrated over the solid angle $(\Delta u_a, \Delta\phi_a)$ of the optical system aperture. In other words, CAT-DISORT was used to solve the forward problem: for given IOPs of the layered tissue: $g(\tau)=\{\alpha(\tau), \sigma(\tau), g(\tau)\}$, predict (simulate) values for the diffuse reflectance spectra (AOPs): $\tilde{f}=\{\tilde{f}_1, \tilde{f}_2, \ldots, \tilde{f}_n, \ldots \tilde{f}_N\}$, where $\tilde{f}_n$ (n=1, 2, ... N) corresponds to the reflected radiance at N different wavelengths, and $\tilde{f}_n=\tilde{f}_n(g)=\int_{\Delta\phi_a} d\phi_a \int_{\Delta M_a} du_a I_n(0, u_a, \phi_a)$.

Simulated data $\tilde{f}$ differ from measured data f because the latter contain a stochastic component $\vec{\epsilon}$, i.e. noise, so that $$f=\tilde{f}(g)+\vec{\epsilon}. \quad (7)$$

The covariance matrix of the noise $C_\epsilon = E\{\vec{\epsilon}\vec{\epsilon}^T\}$ is estimated, where E is the mathematical expectation operator. The superscript $^T$ means transposition, so that if $\vec{\epsilon}$ denotes a column vector, $\vec{\epsilon}^T$ is the corresponding row vector, and thus $\vec{\epsilon}\vec{\epsilon}^T$ is a symmetric matrix of dimension N×N.

In formulation of an inverse problem, note that the tissue IOPs assembled in the vector g depend on the wavelength of the incident light. Second, tissue model parameters are assembled in a vector s. Thus:

$$s=\{s_1, s_2, \ldots, s_m, \ldots, s_M\}$$

represents M issue MP&PP components (such as the contents of melanosomes, blood, keratin, etc. in the tissue layers). Provided that the spectral signatures of all MP&PP components are known, they can be used to define the IOPs of the tissue:

$$g=g(s).$$

Letting F denote a nonlinear operator that maps a vector of MP&PP tissue components into a vector of simulated measurements, i.e. $\tilde{f}(g)=F(s)$, the model can be rewritten $$f=F(s)+\vec{\epsilon}. \quad (8)$$

Note that the operator F is defined implicitly. It returns a solution of the radiative transfer Eq. (4) for the layered medium with IOPs g, induced by tissue parameters s:g=g(s) and known incident beam $S_b$.

Now, an inverse problem is presented: given N spectral reflectance measurements with a certain level of noise ($\vec{\epsilon}$): $f=F(s)+\vec{\epsilon}$, find M parameters s, which describe the optically important MP&PP components of the tissue.

Even though the number of measurements N is much greater than the number of unknowns M, the inverse problem is still underdetermined (ill-posed). The reason for the ill-posedness is the smoothness of most of the spectral signatures of the MP&PP tissue components, implying that the spectral signature of one MP&PP component can be mimicked by a certain combination of others. This makes it hard if not impossible to find the proper impact of an individual MP&PP component, if the parameterization of the tissue model, in terms of MP&PP components is done without proper analysis of the information content.

To alleviate this problem, a regularization procedure may be invoked. Because the data for the inverse problem contain stochastic noise, Bayesian inference provides a natural way of regularization through the introduction of a probabilistic measure in the space of unknown parameters. From Bayes' theorem on conditional probabilities $$p(f|s)p(s)=p(s|f)p(f)$$

it follows that the conditional probability $p(s|f)$ to get a specific value $s$, when $f$ is given, can be written as $$p(s|f) \propto p(f|s)p(s).$$

If a set of admissible functions $\{s\}$ is defined by the mean value $s_0 = E\{s\}$, and the covariance matrix $C_s = E\{(s-s_0)(s-s_0)^T\}$, then the conditional probability can be represented by the product of two Gaussian distributions. The first one is Gaussian with respect to the noise $\vec{\epsilon} = \tilde{f} - f$, but not with respect to the MP&PP components $s$, because $\vec{\epsilon} = f - F(s)$ contains the nonlinear function $F(s)$. Thus:

$$p(s^o\vec{\sigma}) \propto \exp\left\{-\frac{1}{2}[f - F(s)]^T C_\epsilon^{-1}[f - F(s)]\right\} \times \exp\left\{-\frac{1}{2}(s-s_0)^T C_s^{-1}(s-s_0)\right\} = \exp\left\{-\frac{1}{2}J(s)\right\} \quad (9)$$

If we define the solution $s^*$ as the vector of most probable tissue components, given the vector of measurement $f$, i.e. $p(s^*|f) = \max_s p(s|f)$, then the solution to the inverse problem can be formulated as an optimization: find the vector $s^*$ from a set of admissible vectors $\{s\}$ that yields the optimum (minimum) value of the functional $$J = J(s) = [f - F(s)]^T C_\epsilon^{-1}[F(s) - f][f - F(s)] + (s-s_0)^T C_s^{-1}(s-s_0). \quad (10)$$

Thus, the functional in Eq. (10) (objective function) is the weighted least mean squares difference between simulated and measured radiances, with an extra regularization term (penalty function), represented by the second term in Eq. (10), which is strictly convex and defines the set of admissible tissue component parameters.

An outline of the Gauss-Newton algorithm for nonlinear inversion is now presented. The objective function in Eq. (10) near the reference model $s_0$ in terms of $\tilde{s} = s - s_0$:

$$J(s) = J(s_0 + \tilde{s}) = J(s_0) + \Delta J(\tilde{s}) = \text{const} + \Delta J(\tilde{s}) \quad (11)$$

Assuming that $|\tilde{s}| \ll |s_0|$, an approximate the term $\Delta J(\tilde{s})$ in Eq. (10) by a quadratic form with respect to $\tilde{s}$. Thus, keeping just the constant and the linear term of $F(s)$, is $$F(s) = F(s_0) + \frac{\partial F}{\partial s}\bigg|_{s_0} \tilde{s} + \ldots \equiv F(s_0) + L_0\tilde{s} + \ldots \approx F(s_0) + L_0\tilde{s}. \quad (12)$$

Here the linear operator $L$, stands for the Jacobian $$L_o = \frac{\partial F}{\partial s}\bigg|_{s_0} = \frac{\partial \tilde{f}}{\partial g}\frac{\partial g}{\partial s}\bigg|_{s_0} \quad (13)$$

where the subscript indicates that the reference state $s_0$ is used to evaluate the Jacobian (Frèchet derivative). Similarly, $L_i$ is used for the Frèchet derivatives evaluated at state $s_1$.

The linear approximation in Eq. (12) corresponds to approximating the conditional probability (9) with a Gaussian distribution of unknowns $s$:

$$p(s|f) \propto \exp\left\{-\frac{1}{2}J(s_0)\right\}\exp\left\{-\frac{1}{2}\Delta J(\tilde{s})\right\} \propto \exp\left\{-\frac{1}{2}\Delta J(\tilde{s})\right\}$$

which can be approximated as $$p(s|f) \propto \exp\left\{-\frac{1}{2}[(L_0\tilde{s} - \delta f)^T C_\epsilon^{-1}(L_0\tilde{s} - \delta f) + s^{-T}C_s^{-1}\tilde{s}]\right\} \quad (14)$$

with of $\delta f = f - F(s_0)$. It is easy to check that $$(L_0\tilde{s} - \delta f)^T C_\epsilon^{-1}(L_0\tilde{s} - \delta f) + s^{-T}C_s^{-1}\tilde{s} \equiv (\tilde{s} - \tilde{s}^*)^T \Phi_o(\tilde{s} - \tilde{s}^*) + \Delta(f) \quad (15)$$

where $\Delta(f)$ is a term that depends only on the data $(f)$, $$s^* = \Phi_o^{-1}L_o^T C_\epsilon^{-1}(f - F(s_0)) \quad (16)$$

and $$\Phi_o = L_o^T C_\epsilon^{-1} L_o + C_s^{-1}. \quad (17)$$

Using Eq. (15), we get for the conditional probability in Eq. (14):

$$p(\tilde{s}|f) \propto \exp[-\frac{1}{2}(\tilde{s} - \tilde{s}^*)^T \Phi_o(\tilde{s} - \tilde{s}^*)] \quad (18)$$

which now has the standard form of a Gaussian distribution with the following parameters: the mean value $E\{\tilde{s}\} = \tilde{s}^*$ (which is the same as the most probable one: max $p(\vec{s}|f) = p(\vec{s}^*|f)$, and the covariance matrix $$E\{(\vec{s} - \vec{s^*})(\vec{s} - \vec{s^*})^T\} = [(\Phi_0)]^{-1} = [L_0^T C_\epsilon^{-1} L_0 + C_S^{-1}]^{-1}. \quad (19)$$

Hence, Eq. (16) provides an explicit form of the solution $s^*$. Thus, no matter which specific algorithms one applies to solve the linearized version of the optimization problem (11), one should arrive at the solution given by Eq. (16) with uncertainties given by Eq. (19).

As soon as $s^*$ is obtained, the corrected reference model becomes $$s_1 = s_0 + s^*$$

and the procedure can be repeated with models $S_1$, $S_2$, ..., until the misfit between simulated and measured data reaches the level of the noise in the data.

The uncertainties in the final solution are given by covariance matrix $[\Phi_{final}]^{-1}$, and the diagonal elements of this matrix give us an estimate of the dispersions of the corresponding tissue model components.

In defining a lesion, the morphological image analysis is based on the logarithm of the measured bidirectional reflectance distribution function $\rho$, defined as:

$$\rho = \ln\left(\frac{L_r}{F_i}\right) \quad (20)$$

where $L_r$ is the reflected intensity or radiance and $F_i$ is the incident lamp flux or irradiance.

The computed morphological parameters are defined as follows:

Lesion border: The border of a lesion is defined from the reflected intensity of the image from one of the visible channels, for example the green channel, looking straight down on the lesion, by identifying the regions in which the gradient of the reflected intensity has its largest values.

Size: The size parameter $p_{M1}$ is defined as the number of pixels comprising the lesion, i.e. $p_{M1}$ the number of pixels inside the lesion border defined above.

Histogram width: Let $h(\rho)$ be the number of pixels having reflectance values between $\rho$ and $\rho+\Delta\rho$. We then define the width parameter $p_{M2}$ of the lesion histogram as $$p_{M2} = \frac{1}{H}\int_{-\infty}^{\rho_l} h(\rho)\sqrt{(\rho-\bar{\rho})^2}\, d\rho \tag{21}$$

where $\rho_l$ defines the lesion border, $H=\int_{-\infty}^{\rho_l} h(\rho)d\rho$, and $$\bar{\rho} = \frac{1}{H}\int_{-\infty}^{\rho_l} \rho h(\rho)d\rho.$$

Moment of inertia: The "center of mass" of a lesion is $$r_M = \frac{\sum_{ij}\rho_{ij} r_{ij}}{\sum_{ij}\rho_{ij}} \tag{22}$$

where the subscripts i and j denote pixel number i in the x direction and number j in the y direction, and $r_{ij}$ is the vector $r_{ij}=i\hat{e}_x+j\hat{e}_y$. The moment of inertia for rotation around the z axis is given by $$M_z = \frac{1}{N}\sum_{ij}\rho_{ij}(r_{ij}-r_M)^T(r_{ij}-r_M), \tag{23}$$

where N is the number of pixels and the superscript T denotes the transpose. Let $h_c$ and $r_c$ be defined as respectively the height and radius of a cylinder with the same "volume" $V=\int_A \rho da$ and area A as the lesion, so that $$h_c = \frac{V}{\pi r_c^2}\quad r_c = \sqrt{\frac{A}{\pi}}. \tag{24}$$

Then, the moment of inertia parameter is defined as $$P_{M3} = \frac{M_z}{\frac{1}{2}\pi h_c r_c^4} \tag{25}$$

where the denominator is the moment of inertia of the cylinder of radius $r_c$ and height $h_c$ for rotation around its axis. $M_z$ is defined in Eq. (23).

Center distance: Let $a_{ij}=1$ for all $\rho_{ij}<0$ and $a_{ij}=0$ for all $\rho_{ij}=0$ (Note that $\rho$ is zero outside the lesion.). "Geometrical center" of the lesion as $$r_A = \frac{\sum_{ij} a_{ij} r_{ij}}{\sum_{ij} a_{ij}}. \tag{26}$$

The center distance of the lesion is defined as the distance between the "center of mass" of the lesion [Eq. (22)] and the "geometrical center" of the lesion divided by the radius $r_c$ of the cylinder, i.e.

$$p_{M4} = \frac{|r_M - r_A|}{r_c}. \tag{27}$$

Darkness: The darkness parameter is defined as the average value of $\rho$ $$p_{M5} = \frac{\sum_{ij}\rho_{ij}}{\sum_{ij} a_{ij}}. \tag{28}$$

where $a_{ij}$ is equal to 1 inside the lesion and equal to 0 outside it.

Fractal dimension: The fractal dimension parameter $p_{M6}$ is defined as $$p_{M6} = \frac{\ln\alpha - \ln N_b}{\ln s} \tag{29}$$

where $N_b$ is the number of lesion border pixels and s is the pixel size, and $\alpha$ is found by a linear fit to the varying values of $\ln N_b$ and $\ln s$ obtained from successive runs with varying resolution. $p_{M6}$ takes values between 1 and 2 depending on the curliness of the lesion border.

Asphericity: The eigenvalues $\lambda_1$ and $\lambda_2$ of the following matrix give the moment of inertia around the two principal axes of the lesion.

$$M = \frac{1}{N}\sum_{ij}\rho_{ij}(r_{ij}-r_V)(r_{ij}-r_V)^T. \tag{30}$$

Asphericity of the lesion is $$p_{M7} = \frac{\lambda_1}{\lambda_2}. \tag{31}$$

Border length: The border length of a lesion is defined as the ratio of the border length of a circle with the same area as the lesion to the border length of the lesion:

$$p_{M8} = \frac{2\sqrt{\pi p_{M1}}}{N_b} \tag{32}$$

where $p_{M1}$ is the size of the lesion and $N_b$ is the number of border pixels.

Size vs. fractal dimension: The parameter $p_{M9}$ is defined as the size dived by the fractal dimension, i.e. $p_{M9}=p_{M1}/p_{M6}$.

Border length vs. fractal dimension: The parameter $p_{M10}$ is defined as the relative border length dived by the fractal dimension, i.e. $p_{M10}=p_{M8}/p_{M6}$.

Morphology Diagnostic Index for Melanoma: a diagnostic index $I_{Mk}$ for each of the morphological parameters $p_{Mk}$ is $$I_{Mk} = \frac{\ln p_{Mk} - \mu_{Mk}}{\sigma_{Mk}} \quad (33)$$

where $\mu_{Mk}$ and $\sigma_k$ are the mean value and the standard deviation of $\ln p_{Mk}$ for all lesions under consideration.

No element, act, or instruction used in the present disclosure should be construed as critical or essential unless explicitly described as such. In addition, as used herein, the article "a" is intended to include one or more items. Where only one item is intended, the term "one" or similar language is used.

It will be understood that various modifications may be made to the embodiments disclosed herein. Therefore, the above description should not be construed as limiting, but merely as exemplifications of the various embodiments of the present disclosure. Those skilled in the art will envision other modifications within the scope and spirit of the claims appended hereto.

What is claimed is:

1. An optical method for determining morphological parameters and physiological properties of a multilayered, vertically inhomogeneous skin tissue having inherent optical properties that are fixed in each layer, but vary between layers, the method comprising the steps of:
    generating a plurality of reflectance images using an optical transfer diagnosis (OTD) device, said plurality of reflectance images comprising reflectance measurements from above a skin surface for a plurality of different wavelengths from multiple angles of illumination and detection and using the reflectance measurements to determine the morphological parameters and the physiological properties for each layer in a plurality of layers of the multilayered, vertically inhomogeneous skin tissue,
    wherein said OTD device comprises a measurement head comprising a plurality of light-emitting diode (LED) lamps and a plurality of cameras where each of the plurality of LED lamps are placed at a different angle, relative to the skin surface
    wherein determining the morphological parameters comprises using one of the reflectance images of the lesion from a visible channel for:
    determining a lesion border,
    measuring a size of the lesion,
    measuring a histogram-width that gives a measure of inhomogeneity of the reflectance image of the lesion,
    capturing a relative moment of inertia of the lesion,
    determining a center distance representing a physical distance between a geometric center of the lesion and a center of mass of absorptance,
    determining a fractal dimension of the lesion which describes the complexity of its border,
    determining an asphericity of the lesion, and
    determining a relative border length of the lesion, wherein the relative border length is defined as a ratio of a border length of a circle with a same area as the lesion to the border length of the lesion,
    and wherein determining the morphological parameters further comprises, and also wherein determining the physiological properties comprises, using a bio-optical model, radiative transfer modeling, and a non-linear inversion procedure;
    systematically varying input values of the morphological parameters and the physiological properties of the skin tissue while simultaneously varying inherent optical properties, wherein the inherent optical properties are linked to the morphological parameters and the physiological properties of the skin tissue by the bio-optical model,
    computing reflectances by the radiative transfer model for a plurality of different wavelengths and a plurality of different measurement configurations, each with specified directions of illumination and observation until an agreement between the reflectance measurements and reflectances computed by the radiative transfer model reaches a predetermined level of accuracy, and
    obtaining, for each layer in the plurality of layers of the multilayered, vertically inhomogeneous skin tissue, the morphological parameters and the physiological properties returned by the non-linear inversion procedure.

2. The method of claim 1, wherein the bio-optical model is based on established absorption and transmission spectra for known tissue chromophores that relates the morphological parameters and the physiological properties of skin tissue to the inherent optical properties of skin tissue.

3. The method of claim 1, wherein the method is used to discriminate between benign pigmented lesions and malignant melanoma.

4. The method of claim 1, wherein the method is used to discriminate between benign tissue and basal cell carcinoma.

5. The method of claim 1, wherein the method is used to discriminate between benign tissue and squamous cell carcinoma.

6. The method of claim 1, wherein the method is used for beauty care.

7. The method of claim 1, wherein the method is used for forensic medicine.

8. The method of claim 1, wherein the method is used to monitor efficacies of different kinds of treatment.

9. The method of claim 1, wherein the non-linear inversion procedure is based on an optimal estimation theory to solve the inverse problem of quantifying specified morphological parameters and physiological properties of skin tissue.

10. The method of claim 9, wherein the morphological parameters and physiological properties of skin tissue include blood content, percentage blood oxygenation, upper epidermis thickness, lower epidermis thickness, percentage of upper melanosome concentration, percentage of lower melanosome concentration, and percentage of keratin concentration.

* * * * *